United States Patent
Shahid

(10) Patent No.: US 6,284,936 B2
(45) Date of Patent: Sep. 4, 2001

(54) STYRENE MONOMER POLYMERIZATION INHIBITION USING SUBSTITUTED DIHYDROXYARENES AND NITROXIDES

(75) Inventor: Muslim D. Shahid, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/746,975

(22) Filed: Dec. 21, 2000

Related U.S. Application Data

(63) Continuation-in-part of application No. 09/150,488, filed on Sep. 9, 1998, now abandoned.

(51) Int. Cl.[7] .............................. C07C 7/20; B01D 3/34
(52) U.S. Cl. ...................... 585/4; 585/20; 585/24; 585/428; 252/182.29; 252/405; 252/407
(58) Field of Search .................... 252/399, 401, 252/403, 404, 405, 407, 182.29; 585/4, 20, 24, 428

(56) References Cited

U.S. PATENT DOCUMENTS

| | | |
|---|---|---|
| 3,800,002 | 3/1974 | Chikatsu et al. . |
| 4,654,450 | 3/1987 | Miller . |
| 4,670,131 | 6/1987 | Ferrell . |
| 4,774,374 | 9/1988 | Abruscato et al. . |
| 5,157,175 | 10/1992 | Lewis et al. . |
| 5,189,086 | 2/1993 | Galbo . |
| 5,254,760 | 10/1993 | Winter et al. . |
| 5,442,071 | 8/1995 | Galbo et al. . |
| 5,545,782 | 8/1996 | Winter et al. . |
| 5,545,786 | 8/1996 | Winter et al. . |
| 5,583,247 | 12/1996 | Nesvadba et al. . |
| 5,616,774 | 4/1997 | Evans et al. . |
| 5,670,692 | 9/1997 | Nesvadba et al. . |
| 5,728,872 | 3/1998 | Riemenschneider . |
| 5,844,025 | 12/1998 | Cunkle et al. . |
| 5,888,356 | 3/1999 | Keil et al. . |
| 5,910,232 | 6/1999 | Hyde et al. . |
| 6,023,000 | 2/2000 | Fritz-Langhals et al. . |
| 6,025,515 | 2/2000 | Shahid . |

FOREIGN PATENT DOCUMENTS

| | | |
|---|---|---|
| 0 791 573 A1 | 8/1997 | (EP) . |
| WO 97/33952 | 9/1997 | (WO) . |
| WO 98/13346 | 4/1998 | (WO) . |

OTHER PUBLICATIONS

WPI Database Abstract, Section Ch, Week 29 1993, Derwent Publications Ltd., London, GB; AN 1993–232479.

PCT International Search Report for PCT/US99/20529, Dec. 20, 1999.

*Primary Examiner*—Joseph D. Anthony
(74) *Attorney, Agent, or Firm*—Madan, Mossman & Sriram, P.C.

(57) ABSTRACT

It has been discovered that the polymerization of vinyl aromatic compounds, such as styrene, may be inhibited by the addition of a composition that contains an alkyl-dihydroxyarene, a hydrogen transfer agent, and a stable nitroxide. In another, preferred embodiment of the invention, these three components are blended in an organic amine.

16 Claims, No Drawings

US 6,284,936 B2

STYRENE MONOMER POLYMERIZATION INHIBITION USING SUBSTITUTED DIHYDROXYARENES AND NITROXIDES

CROSS-REFERENCE TO RELATED APPLICATION

This application is a continuation-in-part application of pending U.S. Pat. application Ser. No. 09/150,488, filed Sep. 9, 1998.

FIELD OF THE INVENTION

The present invention relates to methods and compositions for inhibiting the polymerization of vinyl monomers, and more particularly relates, in one embodiment, to methods and compositions for inhibiting the polymerization of vinyl aromatic monomers.

BACKGROUND OF THE INVENTION

It is well known that undesirable and costly polymerization is a significant problem during the manufacturing of various vinyl monomers, particularly vinyl aromatic compounds, such as styrene. Many kinds of inhibitors have been used in the past to minimize this problem. For instance, inhibitors such as diethylhydroxylamine, phenyl-p-phenylenediamines, tert-butyl catechol, and phenothiazine have been used to control polymer formation. During the early 1980s, compounds selected from the groups called alkyl-substituted di-nitro-phenols and nitroso-phenols found widespread use in the styrene industry. However, because such compounds also functioned as insecticides or were dangerous to handle, their use has been discouraged by environmental and government agencies.

Recently, a new class of compounds called stable free radicals is being investigated to replace the nitrophenol products. Although stable free radicals are effective on monomer polymerization, their current cost makes them unattractive. It would be desirable if a composition and method could be devised to overcome some of the problems in using the stable free radical polymerization inhibitors.

SUMMARY OF THE INVENTION

Accordingly, it is an object of the present invention to provide a method and composition to effectively inhibit the polymerization of vinyl aromatic compounds, such as styrene.

It is another object of the present invention to provide a method and composition to effectively inhibit the polymerization of styrene that is less expensive than using stable free radicals exclusively.

Still another object of the invention is to permit use of a composition to effectively inhibit the polymerization of styrene that has little or no environmental concerns.

In carrying out these and other objects of the invention, there is provided, in one form, a composition for inhibiting polymerization of vinyl aromatic compounds that includes an alkyl-dihydroxyarene, a hydrogen transfer agent, and a stable nitroxide.

DETAILED DESCRIPTION OF THE INVENTION

It has been discovered that the combination of substituted alkyl-dihydroxyarenes, a hydrogen transfer agent, and a stable nitroxide is an effective treatment to control styrene monomer polymerization. This treatment protocol is most effective when formulated in an organic amine, although the composition may find effective use without the organic amine.

It is expected that suitable vinyl aromatic monomers that may be polymerization inhibited by the compositions and methods of this invention include, but are not necessarily limited to styrene, substituted styrene, divinylbenzene, vinyltoluene, vinyl naphthalene, polyvinylbenzenes, and isomers thereof. Preferably, the aromatic monomer is styrene.

Alkl-Dihydroxyarenes

Suitable substituted alkyl-dihydroxyarenes for the polymerization inhibiting composition of the invention may include, but are not necessarily limited to, substituted alkyl-dihydroxybenzenes having the formula:

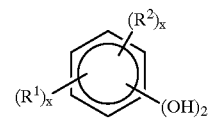

where $R^1$ and $R^2$ are the same or different and are independently selected from the group consisting of hydrogen, straight, branched, and cyclic alkyl groups averaging from about 1 to about 6 carbon atoms, where $R^1$ and $R^2$ are not both hydrogen preferably from about 1 to about 4 carbon atoms, and where x averages from about 1 to about 9.

Examples of specific substituted alkyl-dihydroxyarenes that would be suitable in the composition of this invention include, but are not necessarily limited to, tert-butylhydroquinone; 2,5-di-tert-butylhydroquinone; tert-butylcatechol; hydroquinone; 3,5-di-tert-butylcatechol; catechol; 3,3,3', 3'-tetramethyl-1,1'-spiro-bis-indane-5,5 ', 6,6'-teterol; and mixtures thereof.

Hydrogen Transfer Agent

It is anticipated that any compound that readily transfers hydrogen by an insertion reaction that does not require stable, stand-alone intermediates would be expected to be useful in the invention. The hydrogen transfer agent is a separate component of the inventive composition different from the alkyl-dihydroxyarene. For any particular inventive composition, the alkyl-dihydroxyarene and the hydrogen transfer agent are not the same compound. Hydrogen transfer agents suitable for use in the polymerization inhibiting composition of this invention include, but are not necessarily limited to, naphthalene; anthracene; decalin; hydroquinoline; 1,2,3,4-tetrahydronaphthalene (TETRALIN®; DuPont); 9,10-dihydroanthracene; fluorene; squalane; squalene; trimethyldihydroquinoline, tetramethylhydroquinoline; and mixtures thereof.

Stable Nitroxide

The stable nitroxide of the composition useful for inhibiting polymerization of vinyl aromatic compounds may include, but are not necessarily limited to those having the formula:

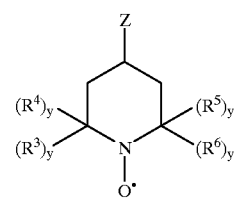

where $R^3$, $R^4$, $R^5$, and $R^6$ are the same or different and are independently selected from the group consisting of straight, branched, or cyclic alkyl groups of from 1 to about 9 carbon atoms, preferably from about 1 to 3 carbon atoms; where y averages from at least 1 to about 6; where Z is selected from the group consisting of hydrogen, oxygen, alkyl groups, alkoxy groups, hydroxyl, aryl groups, alkaryl groups, heterocyclic alkyl groups; and where when Z contains carbon atoms, may contain an average of from about 1 to 9 carbon atoms, preferably from about 1 to 3 carbon atoms.

Examples of specific stable nitroxides that would be suitable in the composition of this invention include, but are not necessarily limited to, 2,2,6,6-tetramethyl-1-piperidinyloxyl (TEMPO); 4-OXO TEMPO; 1-oxyl-2,2,6,6-tetramethylpiperidine; 1-oxyl-2,2,6,6-tetramethylpiperidin-4-one; 1-oxyl-2,2,6,6-tetramethylpiperidin-4-yl-2-acetate; 1-oxyl-2,2,6,6-tetramethyl-1-piperidin-4-yl-2-ethylhexanoate and mixtures thereof.

Organic Amine

Organic amines suitable in the methods and compositions of this invention may include, but are not necessarily limited to, organic amines of the formula:

$$R^7\text{—}NH\text{—}R^8$$

where $R^7$ and $R^8$ are the same or different and are independently selected from the group consisting of straight, branched, and cyclic alkyl groups; alkoxy groups; hydroxyalkyl groups; and aminoalkyl groups; averaging of from about 1 to about 20 carbon atoms, preferably from about 6 to about 9 carbon atoms, where both $R^7$ and $R^8$ are not simultaneously hydrogen.

Examples of specific organic amines that would be suitable in the composition of this invention include, but are not necessarily limited to, butylamine; hexylamine; n-octylamine; dodecylamine; cyclohexylamine; N,N-dihexylamine; ethanolamine; N-(2-aminoethyl)ethanol; ethylenediamine; 2-aminopropanol; and mixtures thereof.

Proportions

A number of factors affect the effective amounts of the alkyl-dihydroxyarenes, hydrogen transfer agents, and stable nitroxides of this invention that would be useful to inhibit the polymerization of a vinyl compound, including, but not necessarily limited to, the nature of the vinyl compound, the concentration of the vinyl compound, the temperature and pressure environment of the vinyl compound, the nature of the particular alkyl-dihydroxyarenes, hydrogen transfer agents, and stable nitroxides used, and the like. Nevertheless, some general guidelines as to the effective proportion of the alkyl-dihydroxyarenes, hydrogen transfer agents, and stable nitroxides in the vinyl compound may be given.

If the organic amine is not present, the composition of this invention may have from about 1 to about 10,000 ppm of the alkyl-dihydroxyarene; from about 1 to about 10,000 ppm of the hydrogen transfer agent; and from about 1 to about 10,000 ppm of the stable nitroxide, based on the total amount of vinyl aromatic compound being treated. Preferably, the proportions range from about 34 to about 200 ppm of the alkyl-dihydroxyarene; from about 34 to about 118 ppm of the hydrogen transfer agent; and from about 34 to about 145 ppm of the stable nitroxide, based on the total amount of vinyl aromatic compound being treated.

If the organic amine is present, then the composition of this invention may have from about 1 to about 10,000 ppm of the alkyl-dihydroxyarene; from about 1 to about 10,000 ppm of the hydrogen transfer agent; from 1 to about 10,000 ppm of the stable nitroxide and from about 1 to about 10,000 ppm of the organic amine, based on the total amount of vinyl aromatic compound being treated. Preferably, the proportions range from about 34 to about 200 ppm of the alkyl-dihydroxyarene; from about 34 to about 118 ppm of the hydrogen transfer agent; from about 34 to about 145 ppm of the stable nitroxide and from about 5 to about 300 ppm of the organic amine, based on the total amount of vinyl aromatic compound being treated.

The components of the composition may be simply mixed together. They may be mixed together in a single composition prior to addition to the vinyl aromatic compound, although they may also be added to the vinyl compound separately.

The invention will be further illustrated with respect to specific examples, which are not intended to limit the invention, but rather to more fully describe it.

Test Method

In order to evaluate the effectiveness of the invention, the following method was employed. It is best to prevent the presence of residual oxygen in the reaction vessels during testing. Oxygen has been shown in the literature and laboratory results to increase the activity of some inhibitors in preventing styrene polymerization.

Inhibited styrene monomer purchased from Aldrich Chemicals was distilled under vacuum (45° C., 29 mm Hg) to remove the conventional storage inhibitor 4-tert-butyl-pyrocatechol. The distilled styrene was checked for polymer content by sampling a portion and mixing in cold methanol. The distillation of the styrene monomer is considered successful if the two liquids mix completely with no presence of haze or cloudy appearance. One hundred mls of distilled styrene was transferred into a 250 ml, three-necked, round bottom reaction flask. The desired amount of inhibitor(s) were added to the distilled styrene monomer. The reaction flask was also equipped with a condenser, a thermocouple (type J), thermometer (Celsius), and a gas sparge tube.

The reaction apparatus was placed in an oil bath. The temperature of the oil bath could be raised by the use of an external heating device. The styrene monomer was purged with nitrogen for 20 minutes to insure that the effect of oxygen on styrene monomer and/or inhibitors would be insignificant during the test run. While continuing the nitrogen purge, the temperature of the oil bath and subsequently, the styrene/inhibitor(s) composition was raised until a styrene monomer/inhibitor(s) composition temperature of 118° C. ±2° C. was obtained. The styrene monomer/inhibitor(s) composition was maintained under these conditions for 90 minutes.

The reaction flask apparatus was removed from the hot oil bath and the styrene monomer/inhibitor(s) composition was allowed to cool to ambient under continuing nitrogen purge. The styrene monomer/inhibitors) composition was transferred from the reaction flask into a 1000 ml beaker containing 200 ml of cold methanol. The styrene/methanol mixture was mixed until the polymer, if any, agglomerates. Eight hundred ml of n-heptane was added to the styrene methanol composition. The polystyrene, if any, was allowed to settle out of solution until the liquid phase of the composition was clear. The styrene/methanol/n-heptane/polymer mixture was filtered through a 1.0 µm glass fiber filter. Any remaining polymer was washed from the beaker with n-heptane through the glass fiber filter paper. The filter paper was placed to an oven with ventilation capable of maintaining a temperature of 150° C. ±2° C. for 3 hours. The dried polymer was cooled in a desiccator, and the weight of the polymer was obtained by taking the difference of the weight of filter paper/polymer minus the initial weight of filter paper. Results were reported as percent polymer formed by weight of polymer formed in mgs divided by the weight of the original styrene monomer used in mg multiplied by 100.

Results

Uninhibited styrene monomer prepared by the above procedure stored at −25° F. (−13° C.) was used to evaluate the additives of the instant invention, as scribed below. As noted, a 90 minute nitrogen reflux test method was used to generate the data. Table I summaries the results from the initial testing.

TABLE I

Polymerization Inhibition Using Various Components

| Ex. | Additive | Concentration (ppm) | Percent Polymer |
|---|---|---|---|
| 1 | none | — | 36 |
| 2 | 4-OH TEMPO[1] | 35 | 14 |
| 3 | 4-OH TEMPO | 125 | 6.0 |
| 4 | 4-OH TEMPO | 150 | 4.0 |
| 5 | 4-OH TEMPO | 500 | 2.6 |
| 6 | 4-Tert-butyl-pyrocatechol | 125 | 14 |
| 7 | TETRALIN[2] | 125 | 18 |
| 8 | Tert-butyl HQ[3] | 125 | 18 |
| 9 | 2,5-Di-tert-butyl HQ | 125 | 16 |

[1]2,2,6,6-Tetramethyl-4-hydroxypiperidine-1-oxyl
[2]1,2,3,4-Tetrahydronaphthalene; this test was stopped after 60 minutes.
[3]HQ = hydroquinone

TABLE II

Polymerization Inhibition Using Various Components
The data below summarizes the results of selected combinations of additives described in the instant invention.

| Ex. | Additive | Concentration (ppm) | Percent Polymer |
|---|---|---|---|
| 19 | 4-OH TEMPO | 35 | 11 |
|  | Tert-butyl HQ | 35 |  |
| 20 | 4-OH TEMPO | 125 | 5.3 |
|  | Tert-butyl HQ | 125 |  |
| 21 | 4-OH TEMPO | 125 | 6.0 |
|  | Tert-butyl-catechol | 125 |  |
| 22 | 4-OH TEMPO | 180 | 5.3 |
|  | Tert-butyl HQ | 180 |  |

TABLE III

Polymerization Inhibition Using Various Components
The data below summarizes the results of selected combinations of additives described in the instant invention formulated in n-octyl amine.

| Ex. | Additive | Concentration (ppm) | Percent Polymer |
|---|---|---|---|
|  | 4-OH TEMPO in n-octyl amine | 125 | 5.0 |
| 24 | 4-OH TEMPO | 125 | 4.0 |
|  | Tert-butyl HQ in n-octyl amine | 125 |  |
| 25 | 4-OH TEMPO | 125 | 4.3 |
|  | DHA[1], in n-octyl amine | 180 |  |
| 26 | 4-OH TEMPO | 125 | 0.42 |
|  | 2,5-di-tert-butyl HQ in n-octyl amine |  |  |

[1]9,10-Dihydroanthracene

TABLE IV

Polymerization Inhibition Using Various Components
The data below summarizes the results of multiple combinations of additives of the invention formulated in n-octyl amine.

| Ex. | Additive | Concentration (ppm) | Percent Polymer |
|---|---|---|---|
| 27 | 4-OH TEMPO | 125 | 0.93 |
|  | DHA | 180 |  |
|  | Tert-butyl HQ | 180 |  |
| 28 | 4-OH TEMPO | 125 | 0.24 |
|  | TETRALIN | 103 |  |
|  | 2,5-di-tert-butyl HQ | 174 |  |
| 29[1] | 4-OH TEMPO | 125 | 0.12 |
|  | TETRALIN | 103 |  |
|  | 2,5-di-tert-butyl HQ | 174 |  |
| 30 | 4-OH TEMPO | 125 | 0.77 |
|  | TETRALIN | 103 |  |
|  | 2,5-di-tert-butyl HQ | 174 |  |

TABLE V

Example 31
The data below summarizes the amount of polymer formed during the duration of the test when using the combination of inhibitors: 125 ppm 4-OH TEMPO, 103 ppm TETRALIN, and 174 ppm 2,5-di-tert-butyl HQ all formulated in n-octylamine. The test apparatus is equipped with a septum and a 5 ml sample is extracted with a syringe at designated time intervals.

| Time | Percent Polymer |
|---|---|
| 0 | 0 |
| 15 | 0 |
| 30 | 0 |
| 45 | 0 |
| 60 | 0 |
| 75 | 0.05 |
| 90 | 0.15 |

[1]This Example was formulated in n-(2-aminoethyl)ethanol instead of n-octyl amine.

TABLE VI

Example 32
The data below summarizes the amount of polymer formed during the duration of the test when using the combination of inhibitors: 52 ppm TETRALIN, 87 ppm 2,5-di-tert-butyl HQ, and 65 ppm 4-OH TEMPO formulated in n-octylamine. Samples were extracted as in Example 31.

| Time | Percent Polymer |
|---|---|
| 0 | 0 |
| 15 | 0 |
| 30 | 0 |
| 45 | 0 |
| 60 | 0.1 |
| 75 | 0.62 |
| 90 | 1.2 |

TABLE VII

Example 33
Table VII shows that even when the di-hydroxyarene compound is not formulated in an organic amine the combinations of stable free radical, hydrogen transfer agent and di-hydroxyarene materials are still quite effective.

| Additive | Concentration (ppm) | Percent Polymer |
| --- | --- | --- |
| 4-OH TEMPO | 125 | 0.64 |
| TETRALIN | 103 | |
| 2,5-di-tert-butyl HQ | 174 | |

TABLE VIII

Polymerization Inhibition Using Various Components
A 1000 ml of inhibited styrene monomer was distilled under vacuum and the freshly distilled styrene monomer material was immediately used to evaluate the instant invention. All the inhibitors are formulated with n-octyl amine.

| Ex. | Additive | Concentration (ppm) | Percent Polymer |
| --- | --- | --- | --- |
| 34 | 4-OH TEMPO | 125 | 0.06 |
| | TETRALIN | 103 | |
| | 2,5-di-tert-butyl HQ | 174 | |
| 35 | 4-OH TEMPO | 125 | 0.06 |
| | DHA | 140 | |
| | 2,5-di-tert-butyl HQ | 174 | |

The results indicate that the instant invention is even more effective on controlling polymer formation when using freshly distilled styrene.

In the foregoing specification, the invention has been described with reference to specific embodiments thereof, and has been demonstrated as effective in providing a composition for inhibition of polymerization of vinyl aromatic compounds, such as styrene. However, it will be evident that various modifications and changes can be made thereto without departing from the broader spirit or scope of the invention as set forth in the appended claims. Accordingly, the specification is to be regarded in an illustrative rather than a restrictive sense. For example, specific combinations of components, other than those specifically tried, in other proportions or ratios or added in different ways, falling within the claimed parameters, but not specifically identified or tried in a particular composition to improve the polymerization inhibition herein, are anticipated to be within the scope of this invention.

I claim:

1. A method for inhibiting polymerization of vinyl aromatic compounds comprising:
   providing a vinyl aromatic compound; and adding thereto an amount effective to inhibit polymerization of the vinyl aromatic compound of a composition comprising:
   a. an alkyl-dihydroxyarene;
   b. a hydrogen transfer agent different from the alkyl-dihydroxyarene, wherein said hydrogen transfer agent is selected from the group consisting of naphthalene, decalin, hydroquinoline, 1,2,3,4-tetrahydronaphthalene, 9,10-dihydroanthracene, fluorene, squalane, squalene, trimethyldihydroquinoline, tetramethylhydroquinoline, and mixtures thereof; and
   c. a stable nitroxide.

2. The method of claim 1 where in the adding, in the composition, the alkyl-dihydroxyarene has the formula:

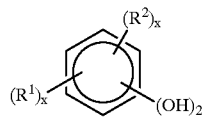

where $R^1$ and $R^2$ are the same or different and are independently selected from the group consisting of hydrogen, straight, branched, and cyclic alkyl groups averaging from about 1 to about 6 carbon atoms where $R^1$ and $R^2$ are not both hydrogen, and where x averages from at least 1 to about 9.

3. The method of claim 1 where in the adding, in the composition the stable nitroxide has the formula:

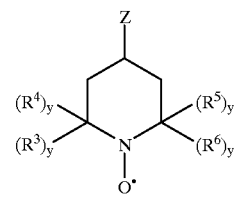

where $R^3$, $R^4$, $R^5$, and $R^6$ are the same or different and are independently selected from the group consisting of straight, branched, or cyclic alkyl groups of from 1 to about 9 carbon atoms; where y averages from at least 1 to about 6; where Z is selected from the group consisting of hydrogen, oxygen, alkyl groups, alkoxy groups, hydroxyl, aryl groups, alkaryl groups, heterocyclic alkyl groups; and when Z contains carbon atoms, contains an average of from about 1 to 9 carbon atoms.

4. The method of claim 1 where in the adding, in the composition the components have the following proportions:
   from about 1 to about 10,000 ppm of the alkyl-dihydroxyarene;
   from about 1 to about 10,000 ppm of the hydrogen transfer agent; and
   from about 1 to about 10,000 ppm of the stable nitroxide, based on the total amount of vinyl aromatic compound being treated.

5. The method of claim 1 where in the adding, the composition further comprises an organic amine.

6. The method of claim 5 where in the adding, in the composition the organic amine has the formula:

$$R^7\text{—NH—}R^8$$

where $R^7$ and $R^8$ are the same or different and are independently selected from the group consisting of straight, branched, and cyclic alkyl groups; alkoxy groups; hydroxyalkyl groups; and aminoalkyl groups; averaging of from about 1 to about 20 carbon atoms, where both $R^7$ and $R^8$ are not simultaneously hydrogen.

7. The method of claim 5 where in the adding, in the composition, the organic amine is present in the total amount of vinyl aromatic compound being treated in an amount ranging from about 1 to about 10,000 ppm.

8. A polymerization inhibited vinyl aromatic composition comprising:
   a. an alkyl-dihydroxyarene;
   b. a hydrogen transfer agent different from the alkyl-dihydroxyarene, wherein said hydrogen transfer agent is selected from the group consisting of naphthalene, decalin, hydroquinoline, 1,2,3,4-tetrahydronaphthalene, 9,10-dihydroanthracene, fluorene, squalane, squalene, trimethyldihydroquinoline, tetramethylhydroquinoline, and mixtures thereof;

c. a stable nitroxide; and d. a vinyl aromatic compound.

9. The composition of claim 8 where the components have the following proportions:

from about 1 to about 10,000 ppm of the alkyl-dihydroxyarene;

from about 1 to about 10,000 ppm of the hydrogen transfer agent; and from about 1 to about 10,000 ppm of the stable nitroxide, based on the total amount of vinyl aromatic compound being treated.

10. The composition of claim 8 further comprising an organic amine.

11. The composition of claim 8 where the organic amine is present in the total amount of vinyl aromatic compound being treated in an amount ranging from about 1 to about 10,000 ppm.

12. The composition of claim 8 where the vinyl aromatic compound is styrene.

13. A composition for inhibiting polymerization of vinyl aromatic compounds comprising:

a. an alkyl-dihydroxyarene;

b. a hydrogen transfer agent different from the alkyl-dihydroxyarene, wherein said hydrogen transfer agent is selected from the group consisting of naphthalene, decalin, hydroquinoline, 1,2,3,4-tetrahydronaphthalene, 9,10-dihydroanthracene, fluorene, squalane, squalene, trimethyldihydroquinoline, tetramethylhydroquinoline, and mixtures thereof; and c. a stable nitroxide.

14. The composition of claim 13 where the alkyl-dihydroxyarene has the formula:

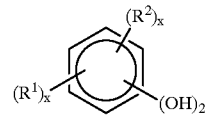

where $R^1$ and $R^2$ are the same or different and are independently selected from the group consisting of hydrogen, straight, branched, and cyclic alkyl groups averaging from about 1 to about 6 carbon atoms where $R^1$ and $R^2$ are not both hydrogen, and where x averages from at least 1 to about 9.

15. The composition of claim 13 where the stable nitroxide has the formula:

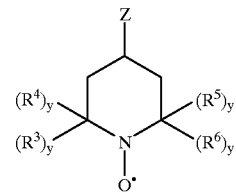

where $R^3$, $R^4$, $R^5$, and $R^6$ are the same or different and are independently selected from the group consisting of straight, branched, or cyclic alkyl groups of from 1 to about 9 carbon atoms; where y averages from at least 1 to about 6; where Z is selected from the group consisting of hydrogen, oxygen, alkyl groups, alkoxy groups, hydroxyl, aryl groups, alkaryl groups, heterocyclic alkyl groups; and when Z contains carbon atoms, contains an average of from about 1 to 9 carbon atoms.

16. The composition of claim 13 further comprising an organic amine having the formula:

$R^7$—NH—$R^8$ where $R^7$ and $R^8$ are the same or different and are independently selected from the group consisting of straight, branched, and cyclic alkyl groups; alkoxy groups; hydroxyalkyl groups; and aminoalkyl groups; averaging of from about 1 to about 20 carbon atoms, where both $R^7$ and $R^8$ are not simultaneously hydrogen.

* * * * *

UNITED STATES PATENT AND TRADEMARK OFFICE
CERTIFICATE OF CORRECTION

PATENT NO. : 6,284,936 B2  Page 1 of 1
DATED : September 4, 2001
INVENTOR(S) : Muslim D. Shahid It is certified that error appears in the above-identified patent and that said Letters Patent is hereby corrected as shown below:

Column 2,
Line 46, delete "anthracene;".

Column 4,
Line 52, delete "/inhibitors)" and insert therefor -- /inhibitor(s) --.
Line 63, delete " to" and insert therefor -- into --.

Column 5,
Line 11, delete "scribed" and insert therefor -- described --.
Line 44, in Table II delete "Tert-butyl-catechol" and insert therefor
-- 4-Tert-butyl-catechol --.
Line 57, in Table III, under Ex. insert -- 23 -- before 4-OH.
Line 64, in Table III, under Concentration (ppm) insert -- 125 --.

Column 6,
Line 22, in Table IV, delete "4-OH TEMPO" and insert therefor
-- 4-OXO TEMPO --.

Signed and Sealed this

Twenty-seventh Day of August, 2002

Attest:

JAMES E. ROGAN
Attesting Officer  Director of the United States Patent and Trademark Office